United States Patent
Harrington

[11] Patent Number: 5,815,627
[45] Date of Patent: Sep. 29, 1998

[54] CO-AXIAL HOLLOW CORE WAVEGUIDE

[75] Inventor: James A. Harrington, Martinsville, N.J.

[73] Assignee: Rutgers, The State University of New Jersey, Piscataway, N.J.

[21] Appl. No.: 730,116

[22] Filed: Aug. 8, 1996

Related U.S. Application Data

[60] Continuation-in-part of Ser. No. 512,672, Aug. 8, 1995, Pat. No. 5,567,471, which is a division of Ser. No. 181,852, Jan. 13, 1994, Pat. No. 5,440,664.

[51] Int. Cl.⁶ ........................................................ G02B 6/20
[52] U.S. Cl. ........................................... 385/125; 385/141
[58] Field of Search ................................... 385/125, 141, 385/142

[56] References Cited

U.S. PATENT DOCUMENTS

| | | | |
|---|---|---|---|
| 4,372,648 | 2/1983 | Black | 385/125 |
| 4,453,803 | 6/1984 | Hidaka et al. | 385/125 |
| 4,652,083 | 3/1987 | Laakmann | 385/125 |
| 4,688,892 | 8/1987 | Laakmann | 385/125 |
| 4,688,893 | 8/1987 | Laakmann | 385/125 |
| 4,778,249 | 10/1988 | Worrell | 385/125 |
| 4,805,987 | 2/1989 | Laakmann et al. | 385/125 |
| 4,913,505 | 4/1990 | Levy | 350/96.1 |
| 4,930,863 | 6/1990 | Croitoriu et al. | 385/125 |
| 5,005,944 | 4/1991 | Laakmann et al. | 385/125 |
| 5,030,217 | 7/1991 | Harrington | 606/14 |
| 5,325,458 | 6/1994 | Morrow et al. | 385/125 |
| 5,395,480 | 3/1995 | Bhardwaj et al. | 156/626 |
| 5,440,664 | 8/1995 | Harrington et al. | 385/125 |
| 5,470,330 | 11/1995 | Goldenberg et al. | 606/7 |
| 5,567,471 | 10/1996 | Harrington et al. | 427/163.2 |

*Primary Examiner*—John D. Lee
*Assistant Examiner*—Ellen E. Kang
*Attorney, Agent, or Firm*—Fish & Richardson P.C.

[57] ABSTRACT

A rugged flexible hollow-fiber waveguide that permits preservation of good transverse spatial coherence of input infrared laser radiation and that transmits substantial power of such radiation, with low attenuation. The present invention preferably comprises a small-diameter thin-wall silica-glass tube; a protective coating on the outer surface of the tube; a sufficient reflective layer on the inner surface of the tube; and a thickness, optimal for the wavelength(s) of interest, of dielectric on the exposed surface of the reflective layer. The fiber is manufactured with processes that maintain the smoothness of the bore. In addition to transmitting mid-infrared laser radiation through the bore of the flexible hollow-fiber waveguide, a second beam may be transmitted through the annular body of the flexible hollow-fiber. The second beam may comprise an aiming beam which creates a ring pattern surrounding the infrared beam, or the second beam may be a second therapeutic beam in the visible or near infrared region.

32 Claims, 11 Drawing Sheets

CO-AXIAL HOLLOW CORE WAVEGUIDE

CROSS REFERENCE TO RELATED APPLICATION

This is a continuation-in-part of application Ser. No. 08/512,672, now patented with U.S. Pat. No. 5,567,471, filed Aug. 8, 1995, which is a divisional of Ser. No. 08/181,852 now U.S. Pat. No. 5,440,664 filed Jan. 13, 1994.

BACKGROUND OF THE INVENTION

1. Field of the Invention

This invention relates to waveguides for transmitting electromagnetic radiation, and more particularly to a dual hollow core flexible fiber waveguide for transmitting a plurality of beams of electromagnetic radiation.

2. Description of Related Art

Radiation from visible, near-ultraviolet, and near-infrared lasers is transmitted well by simple, robust, inexpensive, nontoxic, solid oxide-glass fibers. However, a problem persists in devising a delivery system for transporting radiation from a mid-infrared laser to the point where application of that radiation is desired. Laser emissions at these wavelengths are not transmitted well by most solids. Whether the use be industrial or surgical, a satisfactory delivery system for mid-infrared should: (1) allow focal-spot sizes under 0.5 mm (preferably down to 0.1 mm) in diameter, at a reasonable working distance for the particular use, without requiring a large final optic; (2) transmit at least several tens of watts of average power, with low attenuation; (3) be easily maneuvered about an application site, with little resistance to motion and with minimal bulk to impair access to and viewing of the application site, and without substantial change in the output characteristics; and (4) be simple, robust, and relatively inexpensive. For surgical applications, the delivery system also must not itself be hazardous to the patient (such as are fibers containing toxic materials that are soluble in body fluids). It will be appreciated by those skilled in the art of laser application, that the requirements for good focusability and for unchanging output characteristics necessarily imply that the laser operate in the Gaussian or $TEM_{00}$ mode and that the delivery system not substantially degrade that mode.

For the laser wavelengths of immediate present interest (roughly, 2.5–12 $\mu$m), hitherto there has been no satisfactory delivery system. Articulated arms provide good beam quality and good transmission, but are awkward, complex, and expensive, and require frequent realignment. Solid fibers for this wavelength region provide poor beam quality and only fair transmission, are generally toxic, are expensive, and can be bent only a very limited number of times and to a rather limited degree. Accordingly, the art has attempted to use hollow waveguide fibers.

Prior-art hollow n>1 waveguides provide poor beam quality (poor transverse spatial coherence). FIG. 12B of Gregory & Harrington, and FIGS. 5 and 6 of Croitoru et al., "Characterization of hollow fibers for the transmission of infrared radiation", Appl. Opt. v. 29, 1805–1809 (20 Apr., 1990) and Dror et al., "Hollow Tubes for Transmitting IR Laser Energy for Surgery Applications", presented to ICALEO '89 (15–20 Jan., Los Angeles), are representative of the characteristics of prior art hollow n>1 waveguides. Such waveguides have only fair transmission. Typically, waveguides such as are disclosed in Matsuura & Miyagi, "Low-loss metallic hollow waveguides coated with durable and nontoxic ZnS", Appl. Phys. Lett. v. 61, 1622–1623 (5 Oct., 1992) are superior. Waveguides with metal tube walls which serve as the supporting structure for any coatings (such as disclosed in U.S. Pat. No. 5,005,944, issued to Laakman et al., and U.S. Pat. No. 4,913,505, issued to Levy '505) may be capable of handling substantial power, but are semiflexible at best. Those with plastic tube walls (such as disclosed in U.S. Pat. No. 4,930,863, issued to Croitoru et al.) are flexible, but have marginal power-handling capability at best, high loss, and lack coherence. As such they are suitable principally for signal-handling. Yet-earlier devices such as disclosed in U.S. Pat. No. 3,436,141, issued to Comte, U.S. Pat. No. 3,583,786, issued to Marcatili, and U.S. Pat. No. 3,963,828, issued to Onoda et al., have not proven useful for the applications of present interest at the wavelengths of present interest.

Hollow waveguide fibers having an index of refraction less than one, have not yet attained both transmission characteristics and flexibility required for many applications. However, in other respects these waveguide fibers are quite satisfactory at selected wavelengths. See Gregory & Harrington, "Attenuation, modal, and polarization properties of n<1, hollow dielectric waveguides", Appl. Opt. v. 32, 5302–5309 (20 Sept., 1993).

The present invention provides a waveguide, and method for making such waveguide, that meets the need for a flexible mid-infrared laser transmission medium which has relatively low loss and transmits the laser radiation without disruption of the $TEM_{00}$ mode.

Because of the above-discussed limitations in prior waveguides for mid-infrared laser wavelengths, the use of $CO_2$ lasers in fields such as medicine has been limited. As a result, other types of lasers, which are deliverable via a flexible, solid fibers, have been adopted as alternatives. These include, for example, Nd:YAG, Argon-ion, and other lasers which deliver electromagnetic radiation in the near infrared (0.25–2.5 $\mu$m) and visible ranges. Accordingly, a number of surgical procedures utilizing lasers in these wavelengths have been developed. Since solid fiber waveguides are not effective in transmitting mid-infrared radiation, such as that from $CO_2$ and Er:YAG lasers, there is currently no single laser delivery system capable of transmitting both mid-infrared and near infrared to visible lasers. As a result, a duplication of waveguides is necessary: one waveguide for the $CO_2$ and Er:YAG wavelengths, and another waveguide for the Nd:YAG or Argon-ion laser wavelengths. Consequently, there is a need for a single laser delivery system that can deliver a wider range of therapeutic wavelengths. Furthermore, a similar need is developing to deliver two or more therapeutic laser beams, either simultaneously or consecutively, to the target tissue. These therapeutic procedures would be improved if both beams could be delivered via a single delivery system.

The present invention provides a waveguide and method for making a waveguide that meets the need for a single flexible waveguide that transmits both mid-infrared and visible wavelengths.

Because radiation from $CO_2$ and Er:YAG lasers is infrared, it is not visible to the human eye. To provide a means to aim the beam, a second beam of visible light, typically from a He Ne laser, is transmitted coincident with the $CO_2$ beam. This provides a visible spot for a laser aiming and alignment. Visible aiming beams require a separate waveguide when hollow waveguides (and particularly flexible hollow waveguides) are used, because visible light does not transmit efficiently through these waveguides. As a result, an additional waveguide is generally necessary to guide the aiming beam so that it is coincident with the infrared beam. This adds further to the size and cost of the laser delivery system.

A supplementary waveguide is also sometimes needed for illumination of the target spot. However, whether a second waveguide is needed for aiming, illumination or for a second therapeutic beam, aligning the beams is important. It is important that an aiming beam, for example, be aligned perfectly with the IR beam since the user cannot see the IR beam and will rely on the visible aiming beam to direct the IR beam. Misdirecting that beam can have serious consequences. However, maintaining and monitoring the alignment of the aiming beam can be time consuming. Thus, there is a need for a multiple beam laser delivery system that easily maintains perfect alignment of the two beams.

Also, aiming beams should clearly delineate the location of the IR laser beam, accurately, but without obscuring the visibility of the target spot. Yet some aiming beams, such as He Ne lasers can, because of their brightness, partially obscure the visibility of some of the features of the target spot. Thus there is a need for an aiming beam which shows the location of the target spot without reducing the visibility of the spot.

The present invention provides a solution to the above problems.

SUMMARY OF THE INVENTION

The present invention is a flexible hollow-fiber waveguide and a method for making the waveguide. The waveguide can accept substantial average power (e.g., up to about 1000 W) of pulse energy at or about a design wavelength in the spectral region from <2 $\mu$m to about 20 $\mu$m. The power/energy is input into the bore at the proximal end of the waveguide from a $TEM_{00}$ laser, and propagates with low attenuation in a nearly $HE_{11}$ fiber eigenmode to the distal end of the waveguide. At the distal end, the power/energy is emitted as if it were merely the continuation, without significant degradation, of the input $TEM_{00}$ eigenmode. In some embodiments of the present invention, the spatial profile may differ from that at the input.

The present invention is simple, robust, relatively inexpensive to make, and safe for use in medical/surgical applications. A fiber in accordance with the present invention can also accept visible light at its input and transmit a useful amount of that light through the bore, or preferably via the annular wall of the waveguide to the output for visual illumination and/or for assistance in aiming the infrared laser radiation.

The general embodiment of the device of the present invention comprises a hollow flexible tube having a bore less than approximately 2.5 millimeters and having a smooth internal surface. However, in the preferred embodiment, the bore is about 0.5 millimeter. The tube is preferably a commercially available flexible, thin-wall, silica-glass tube, preferably with a protective sheath on the outer surface of the barrel to protect against abrasion and physical degradation. A layer of material that is optically reflective at mid-infrared wavelengths is deposited on the bore surface in such a way that the resulting bore is optically smooth at such wavelengths. A dielectric film is created or deposited on the exposed surface of the reflective layer in such a way that the resulting film is smooth at both the reflective layer interface and at the air interface, and such that the thickness of the dielectric film is appropriate to the design wavelength. The preferred embodiment, described below, uses silver as the reflective layer, and silver iodide as the dielectric. Other embodiments use metals (e.g., gold, copper, aluminum, nickel, platinum, molybdenum, and zinc) as the reflective layer and other dielectrics such as inorganic compounds (e.g., silver bromide and copper iodide, copper selenide, silver sulfide, zinc selenide, and zinc sulfide ). It will be apparent from the background above, and from the description below, that the devices of the present invention preserve and maintain good input beam quality (good transverse spatial coherence), and hence are a qualitative improvement over the prior-art.

The invention also provides a method of making such devices, comprising the steps of: starting with a tube (such as a vitreous tube) having a smooth bore; plating the bore with a reflective layer using solutions and processes that do not degrade the bore's smoothness, and/or from which the reflective layer "levels" to a smooth reflective surface; and creating a dielectric film of the proper thickness on the exposed surface of the reflective layer, using solutions and processes that do not degrade the bore's smoothness.

Another embodiment of the present invention is a dual core waveguide for the transmission of visible, near infrared and mid-infrared radiation, and a method for making the dual core waveguide. This invention accepts the simultaneous, (or consecutive) delivery of infrared light via a hollow waveguide, and of visible or near-infrared light via a transparent annulus which surrounds the hollow waveguide. Furthermore, because of the coaxial nature of the waveguide, the two or more beams transmitted therein will always be aligned, thus avoiding time consuming alignment procedures. Also, since the outer annulus is used to carry the visible aiming beam, the IR beam carried by the hollow core will always be at the center of a ring ("bulls eye") created by the visible beam.

Because the target spot itself is not illuminated, its features are not obscured. Also, the aiming beam can illustrate to the user the size of the target beam because it will generally be inside the ring.

This embodiment of the present invention generally comprises a hollow, flexible tube having an annular body surrounding a bore with a smooth inner wall bore surface. The tube is preferably a commercially available flexible, thin-wall, transparent waveguide tube. It is also preferred to provide a protective sheath on the outer surface of the tube to protect against abrasion and physical degradation. A layer of material that is optically reflective at mid-infrared wavelengths is deposited on the bore surface in such a way that the resulting bore is optically smooth at such wavelengths. In the preferred embodiment, described below, silver is used as the reflective layer.

Because the bore of the flexible tube carries the mid-infrared beam, and the annular body of the flexible tube carries visible or near infrared light, the simultaneous transmission of mid-infrared through visible wavelengths is possible. In a preferred embodiment, a dielectric film is created or deposited on the exposed surface of the reflective layer in such a way that the resulting film is smooth at both the reflective layer interface and at the mirror interface. Also, the thickness of the dielectric film is appropriate to facilitate transmission at the desired wavelengths.

While the annular body of the tube is capable of transmitting wavelengths shorter than mid-infrared to some degree, such transmission is greatly facilitated if the index of refraction at or near the inner and outer surfaces of the annular body is less than it is near the midpoint between these surfaces. This will facilitate total internal reflection within the annular body so less light will be lost by transmission out of the walls of the annular body. Accordingly, in a preferred embodiment, cladding layers which have an index of refraction less than the annular body is applied at the inner and outer walls of the annular body. The protective sheath may then be applied over the outer cladding. Alternatively, the protective sheath is chosen to have an index of refraction less than that inside the annular body, and it serves as the outer cladding. For example, the inner cladding layer may have an index of refraction of n1, the flexible tube annular body may have an index of refraction of n2, and the outer cladding may have an index of refraction of n3, such that n1 and n3 are both less than n2.

The invention also provides a method for making a dual core waveguide comprising the steps of: forming a waveguide tube comprising a transparent annulus; plating the bore of the annulus with at least one reflective layer by contacting the bore surface with a solution; and providing regions of lower index of refraction at or near the outer surfaces of the annulus than at the interior of the annulus.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Figure 1:
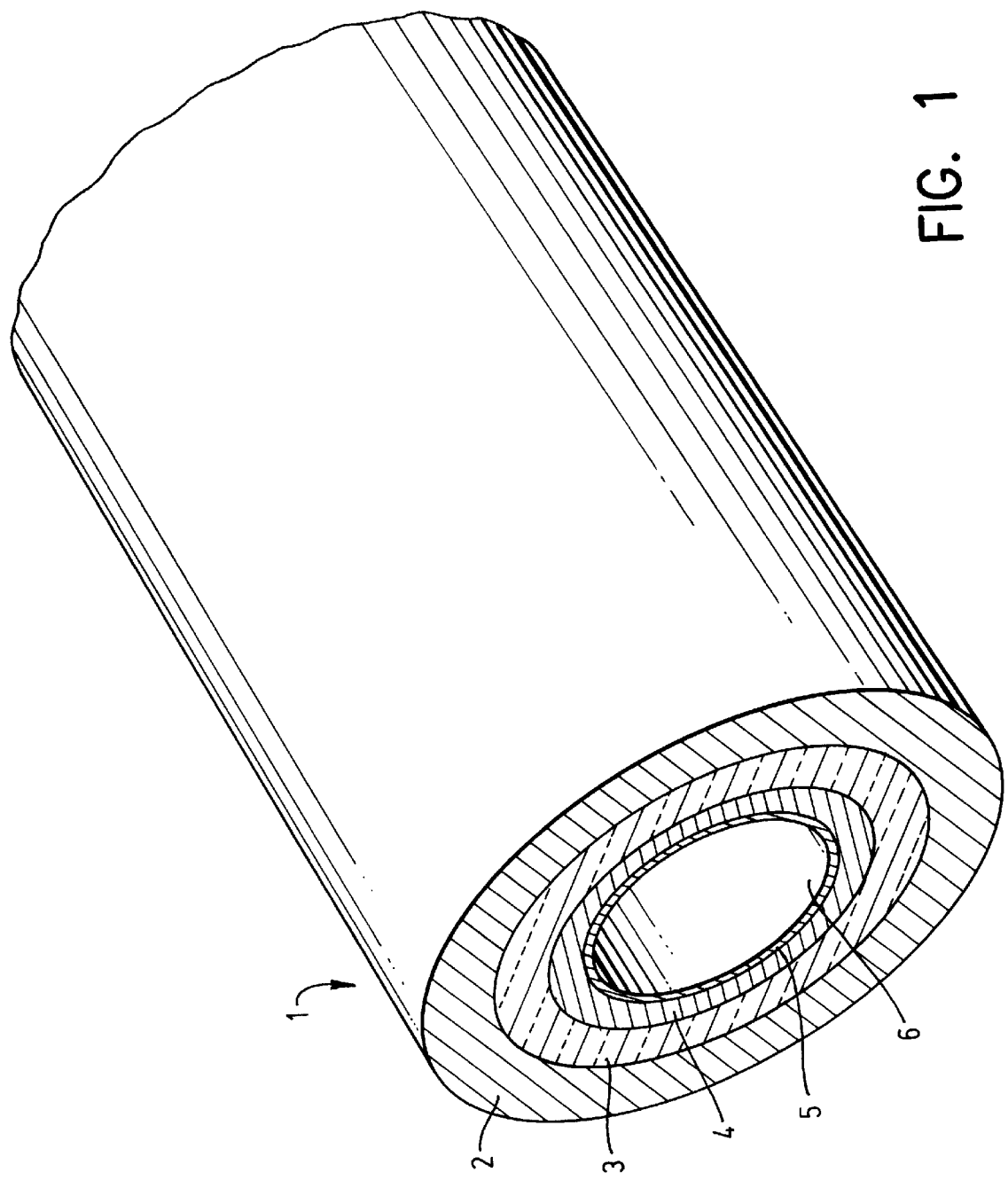
FIG. 1 is a schematic end view of an embodiment of the optical fiber according to the present invention, showing its construction.

FIG. 1 diagrammatically illustrates a hollow-fiber waveguide 1, constructed according to the preferred embodiment of the present invention for transmitting infrared radiation from both incoherent and coherent sources. A protective sheath 2 (which may be a polymer coating, polyamide, silicone/nylon, metal or other material) is preferably formed around or onto the outer surface of the barrel of a hollow-fiber waveguide having a smooth bore, such as a commercially available, thin-wall silica-glass tubing 3. A waveguide 1 of the present invention is preferably of such thickness as to be suited to applications such as carrying cutting radiation to tissue sites within a human body. As such, the tube 3 of the present invention must have an outer diameter that permits the waveguide to be flexible (i.e., easily bent to a radius of less than 10 cm). The sheath 2 preferably protects the tubing from abrasion and other mechanical degradation and seals against moisture and other substances that may physically degrade the tubing 3.

A reflective layer 4 is deposited onto the bore of the tubing 3 in such a way as to retain a smooth exterior surface for the reflective layer 4 or such that the reflective layer 4 "levels" to a smooth reflective surface. The reflective layer is preferably silver of less than 1 $\mu$m in thickness. However, in other embodiments the reflective layer may be of a different thickness. Furthermore, other embodiments may use metals (e.g., gold, copper, aluminum, platinum, molybdenum, zinc, and nickel) and semiconductors (e.g., germanium, etc.) as the reflective layer. A dielectric film 5 preferably having an index of refraction that is less than the index of refraction of the reflective layer 4, is fabricated or deposited (i.e., "created") on the bore of the reflective layer 4 in a manner that substantially retains or improves the smoothness of the exposed surface of the bore. The dielectric film 5 enhances the reflectively of the bore of the waveguide 1. The exact thickness of the dielectric film is determined by optical measurements and is carefully controlled to give the lowest loss at a particular infrared wavelength. Preferably, the dielectric film 5 is approximately 0.1 $\mu$m to 0.8 $\mu$m thick. In the preferred embodiment, the dielectric film is silver iodide. However, in other embodiments, the dielectric film may be inorganic compounds (e.g., silver bromide, copper iodide, copper selenide, silver sulfide, zinc selenide, and zinc sulfide).

The inner exposed surface of the dielectric film 5 defines a preferably hollow interior volume 6 of the waveguide 1, which may contain air, another gas or gaseous mixture, vacuum, or any other medium preferably having an index of refraction that is approximately equal to 1. The reflective layer 4 and the dielectric film are preferably thin and flexible so the final waveguide is essentially a flexible tube with special coatings deposited on the bore to produce a very low loss waveguide at infrared wavelengths. Waveguides in accordance with the present invention may be used to deliver high power (<500 Watts) infrared laser radiation for industrial welding, cutting, and heat treating. The present invention also finds use as broadband infrared fiber sensors operating from approximately 2.0 to 20 $\mu$m. In this role, the waveguides relay infrared signals to remote photo detectors.

In particular, these waveguides could serve as the fiber optic link in remote spectroscopic and radiometric (thermometric) applications.

In the preferred embodiment, the internal diameter of the waveguide 1 prior to the application of the reflective layer 4, is from less than about 1.0 millimeter to about 100 microns, which provides good transmission characteristics, good mechanical flexibility, and is particularly suited for medical uses due to its small size.

In the preferred embodiment, the smoothness of the bore of the tubing 3 prior to finishing is about 0.05 microns or less. The finished waveguide preferably has a similar degree of smoothness. It has been found that such smoothness contributes substantially to the high performance characteristics of the present invention. This degree of smoothness can generally be attained only by glass or glass-like hollow-fiber tubes. However, the invention encompasses any flexible tubing capable of being made with this degree of smoothness.

The spatial profile of the laser beam that is output at the distal end of a waveguide made in accordance with the present invention depends upon the diameter of the bore of the waveguide, the purity of the input laser beam, and the bending radius of the waveguide. Generally, a smaller bore results in a purer mode. Thus, the spatial profile of the laser beam output at the distal end is more similar to the spatial profile of the laser beam input at the proximal end. This is due to the fact that a smaller bore causes higher loss for high-order modes than for lower-order modes. Waveguides having a relatively small bore (for example, approximately less than about 1.0 mm) will best preserve the $TEM_{00}$ mode that is launched into the fiber at the proximal end of the waveguide.

Using the present invention, approximately 3-meter long hollow-fibers can be made having very low attenuation, and high transverse spatial coherence for mid-infrared wavelengths from about 2.0 $\mu$m to about 20 $\mu$m.

EXAMPLE

The smooth-bore, thin-wall, silica-glass tubing 3 (preferably having a protective polymer sheath 2 on the outside) of the preferred embodiment of the present invention is available from several commercial sources (e.g., Fiberguide Industries of Stirling, N.J. and Polymicro Technologies of Phoenix, Ariz.). Glass is preferred because of its high power handling capability (e.g., up to about 500 watts of average power has been demonstrated). The embodiments of the present invention discussed herein have bore diameters of 700, 530, & 320 $\mu$m, but these are presented as exemplars and should not be construed as limiting. Such fibers have a bore roughness of no more than about 0.05 microns. The fibers are preferably used as they are received from a commercial source. Accordingly, no etching procedure is used in the preferred embodiment of the present invention. The bore of the tubing 3 is plated with a reflective layer 4 (such as silver, gold, copper, aluminum, etc.) in a way that maintains the smoothness of the exposed surface of the reflective layer 4. This plating process is described in detail below. Next, a smooth dielectric film 5 (preferably of silver iodide), having a predetermined index of refraction and an optimal thickness for the design wavelength, is formed on the surface of the reflective layer 4. The combination and implementation of these things, in the manner detailed below, is the novel method of the present invention, and produces the novel fiber waveguide 1 of the present invention.

Pretreatment: Etching/Sensitizing/Activating

In one embodiment of the present invention in which silver coatings are used to form the reflective layer 4, the polymer-coated tubing 3 is used as received, with no pretreatment. Pretreatment appears to be part of the reason why prior-art hollow-fibers have not been coherent, since such pretreatment appears to cause the surface of the substrate, and thus the surface of the reflective layer, to be pitted and otherwise coarse (on the scale of optical wavelengths). However, in alternative embodiments in which other metals, such as gold and copper, are used to form the reflective layer 4, pretreatments to the tubing 3 that are standard in the gold and copper coating arts may be required. Pretreatments may also be required before coating the tubing with metals other than silver, gold and copper.

Silver Solution

In accordance with one embodiment of the present invention, a silver solution is produced starting with approximately 1.15 g of 99.999%-pure silver nitrate ($AgNO_3$) dissolved in approximately 400 ml of distilled deionized water ($H_2O$). Aqueous ammonium hydroxide ($NH_4OH$; 15%) is added one drop at a time, causing a brown precipitate to form, and continuing until the solution is clear. A solution of approximately 0.22 g of sodium hydroxide (NaOH) in 100 ml of distilled water is then added to the silver-nitrate/ammonium-hydroxide solution, producing a thick brown precipitate. Ammonium hydroxide is then added one drop at a time until the solution turns clear.

Reducing Solution

A reducing solution is used which consists of approximately 22.5 ml of dextrose ($C_6H_{12}O_6$; 5% by weight in water) diluted to approximately 500 ml with distilled deionized water. Other such reducing solutions are well known in the art and may be used.

Silver Plating

The tubing 3 is preferably laid horizontal or vertical. The silver solution and the reducing solution are preferably combined in approximately equal amounts in a tee-fitting just prior to the inlet to the tubing 3. Depending upon the bore size of the waveguide to be made, as well as the target wavelength, the volume of solution used varies. For $CO_2$ laser wavelengths, a 700-$\mu$m-bore fiber uses approximately 500 ml/2 hrs each of each solution, whereas the 530-$\mu$m and 320-$\mu$m fibers each use approximately 100 ml/1 hr of each solution.

For Er:YAG laser wavelengths, the 700-$\mu$m fiber uses approximately 100 ml/0.5 hr of each solution, and the 530-$\mu$m and 320-$\mu$m fibers each use approximately 50 ml/0.5 hr of each solution. The solutions are forced through the tubing 3 by increasing the pressure at the end of the tube 3 into which the solution enters, such as by a peristaltic pump, or by reducing the pressure at the opposite end of the tube, such as by a vacuum pump. The tubing 3, when horizontal, is preferably turned approximately 180 degrees on its long axis during plating to provide a more uniform coating. In addition or alternatively, the tube ends may be reversed in the middle of the plating procedure, or the solution may be forced through the tube 3 for a predetermined period of time, and subsequently pulled back through the tube 3 for another predetermined period of time, to facilitate more even plating. Furthermore, in accordance with one embodiment of the present invention, the solution may be recirculated for at least some portion of the time the solution flows through the tube 3. The plated tubing 3 is then preferably rinsed with a non-reactive rinsing solution, such as ethanol (ethyl alcohol; $CH_3CH_2OH$), and dried, such as by blowing with compressed air. The quantities of each solution and the rate at which each solution is forced through the bore have been determined empirically.

Iodization

In the preferred embodiment, a solution of approximately 100 ml of cyclohexane, to which 1 g of iodine is added, is mixed in a warm ultrasonic bath. The resulting solution is allowed to cool to approximately room temperature. A quantity of the resulting solution, which depends upon bore size, target wavelength, and type of pump used, is then measured out to form an optimal silver-iodide layer for lowest loss and diffraction-limited (i.e., spatially coherent or gaussian) output. For example, at $CO_2$ wavelengths, for a 700-$\mu$m fiber, approximately 22 ml/5 min. of the iodine/cyclohexane solution is preferably forced through the tubing 3 with a peristaltic pump, or approximately 50 ml/4.5 min. with a vacuum pump. For a 530-$\mu$m fiber, the preferred values are approximately 20 ml/4 min. with a peristaltic pump or approximately 50 ml/4 min. with a vacuum pump. For a 320-$\mu$m fiber, approximately 15 ml/3 min. is preferably used with a peristaltic pump (in this case, a vacuum pump cannot be used because the solution freezes inside the waveguide 1). At the Er:YAG wavelength, a 700-$\mu$m fiber preferably takes approximately 2.5 ml/0.5 min. of solution, using either pump. A 530-$\mu$m fiber preferably takes approximately 4 ml/1 min., using either pump. A 320-$\mu$m fiber, approximately 2.0 ml/0.5 min. is preferably used with a peristaltic pump. In each of the above cases, the pressure must be controlled so that the solution does not freeze. In any case, the resulting tubing 3 is preferably rinsed with a non-reactive rinsing solution, such as ethanol, and dried, such as by blowing with compressed air. The result is a completed waveguide 1. The foregoing should not be construed as limiting. For example, in one alternative embodiment, bromination is effective, and nonpolar solvents with negligible health effects other than cyclohexane may be useful.

DISCUSSION

Figure 2:
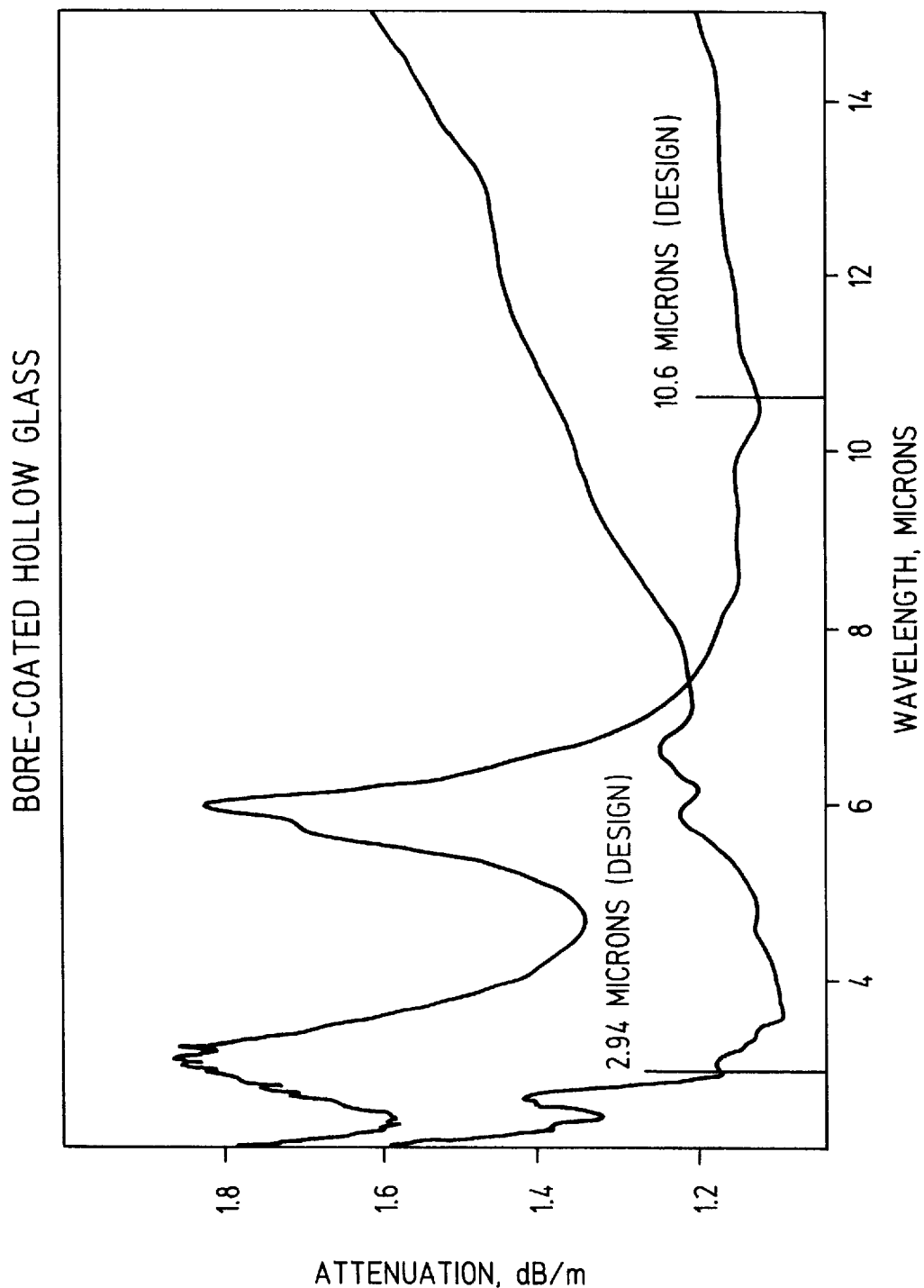
FIG. 2 is a graph of the spectral response of fibers, constructed according to the present invention, for two different design wavelengths.
Figure 3:
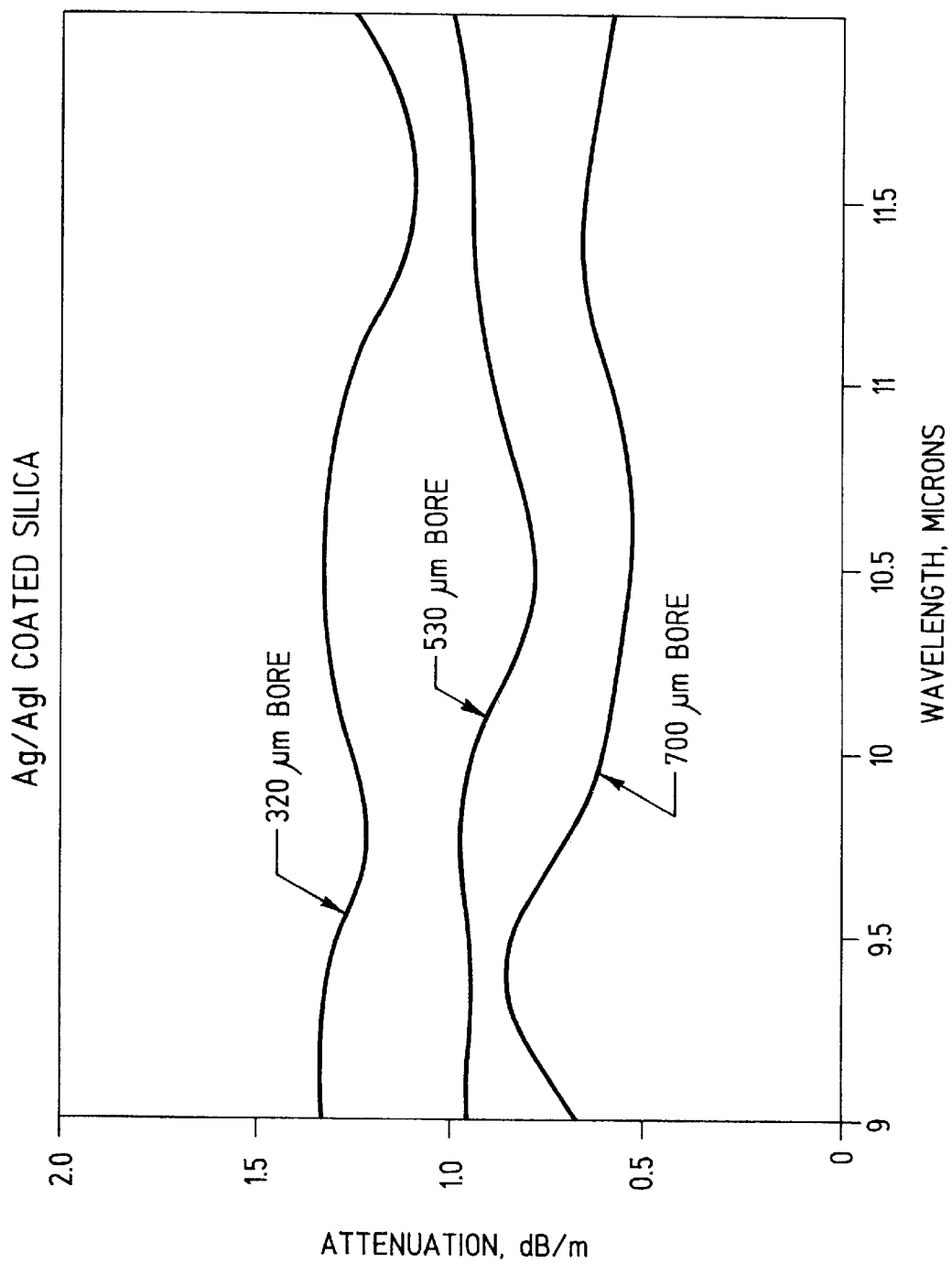
FIG. 3 is a graph of the spectral interference effects for several different fibers constructed according to the present invention.
Figure 8:
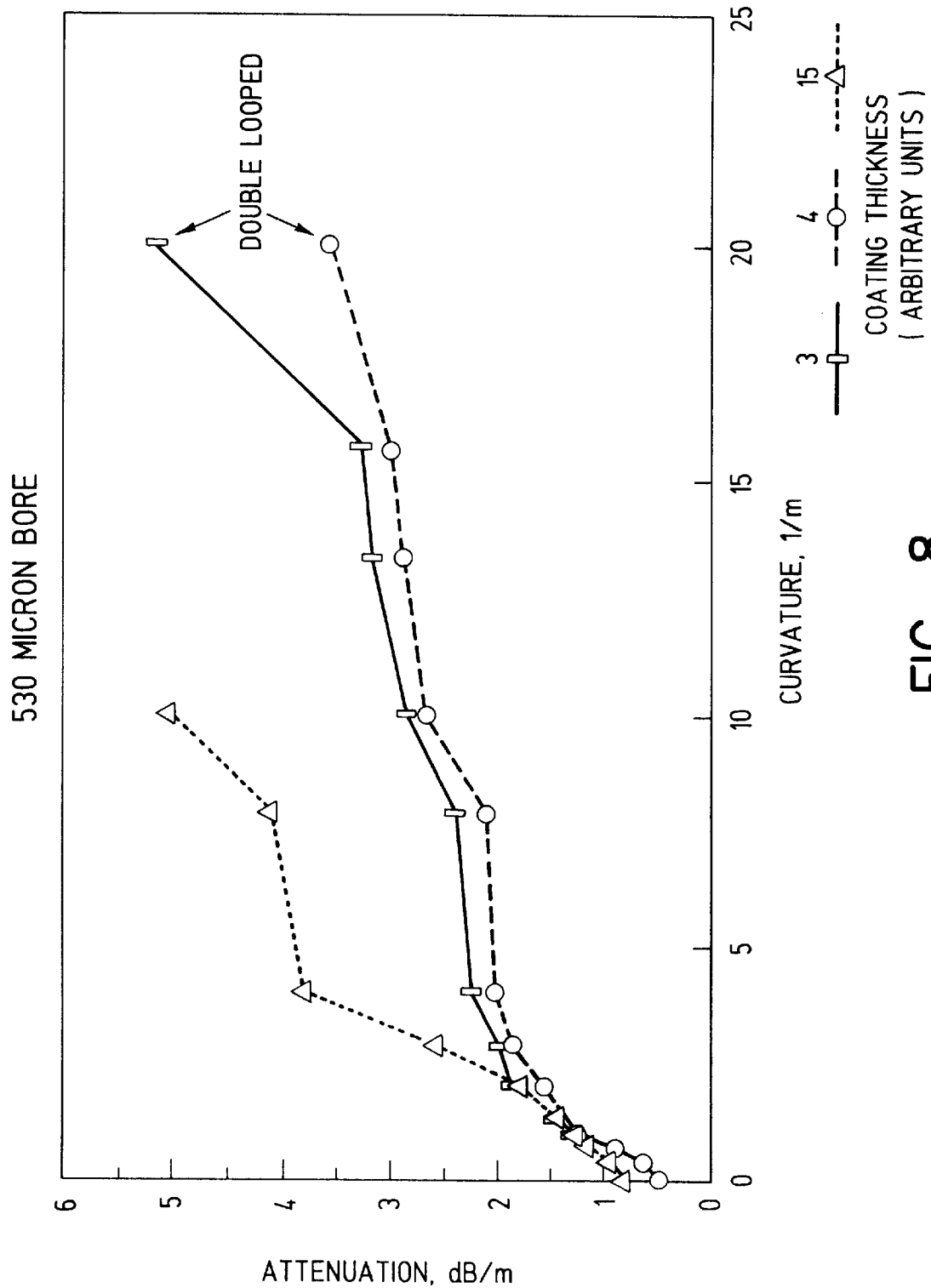
FIG. 8 is a graph illustrating the importance of optimizing and controlling the thickness of the dielectric film, for fibers constructed according to the present invention.

FIGS. 2, 3, and 8 show how the loss is minimized for a chosen spectral region by determining and providing the optimal dielectric film thickness according to the present invention. Proper control of the dielectric film thickness is important to minimizing loss. The present invention allows the thickness of the dielectric film 5 to be precisely controlled, even in small bore fibers.

Figure 4:
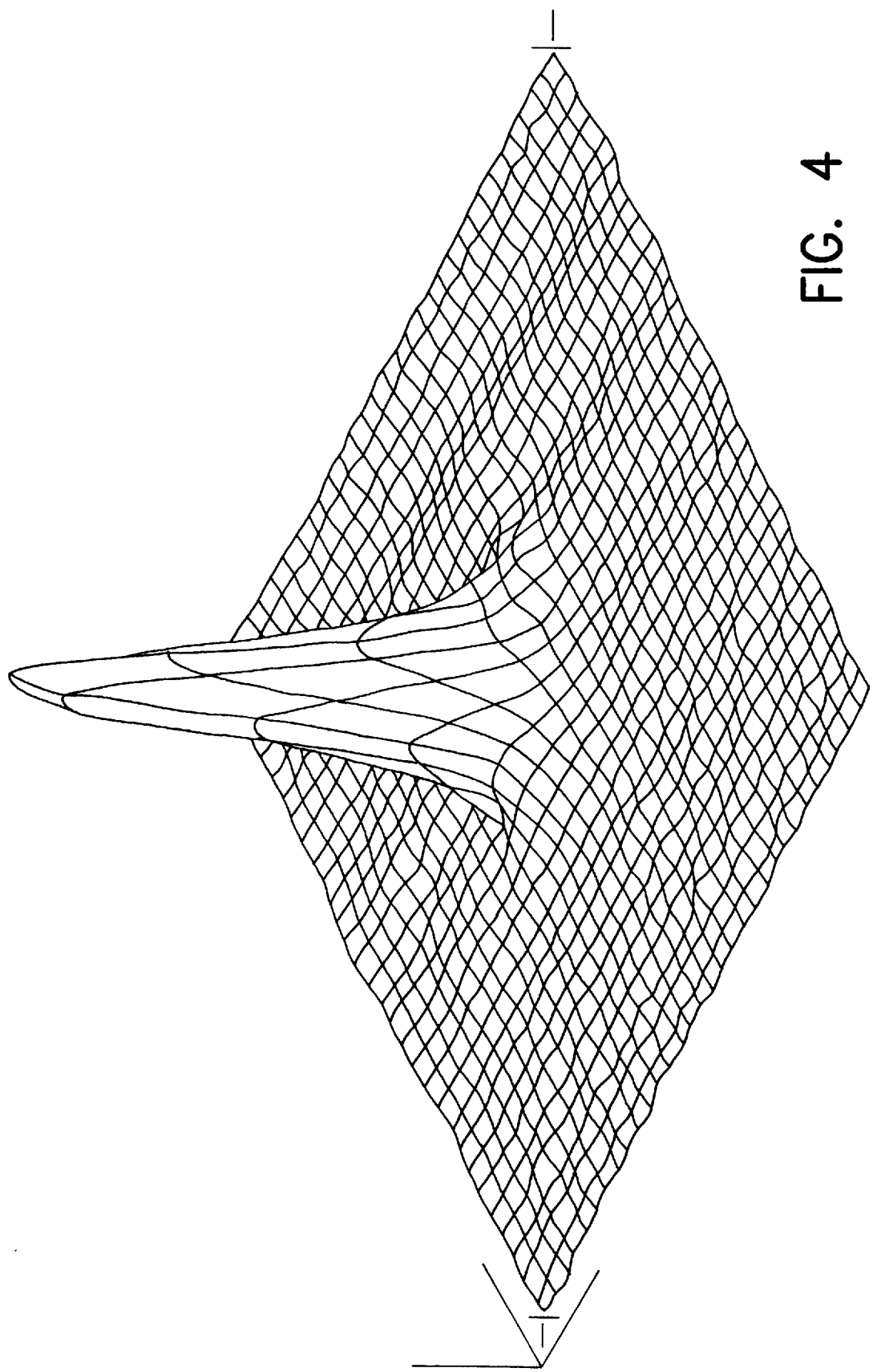
FIG. 4 is a graph of the three-dimensional projection of the spatial profile of the power output from a fiber, constructed according to the present invention, the input of which is correctly illuminated with a $CO_2$ laser.

FIG. 4 demonstrates the excellent mode behavior of waveguides constructed according to the present invention. The output is essentially the same as FIGS. 12A and 13 of Gregory & Harrington (1993), showing that the present method of fabrication does not result in a degraded bore surface. The hollow-fiber waveguides of the present invention are the only such guides with n>1 that do not cause mode-mixing (when initially mode-matched) and consequent multimode output together with excessive bending loss and with substantial changes in output profile as the radius of curvature changes. The importance of the smoothness of the waveguide bore is not taught in the prior art, and such smoothness was not previously attainable.

Figure 5:
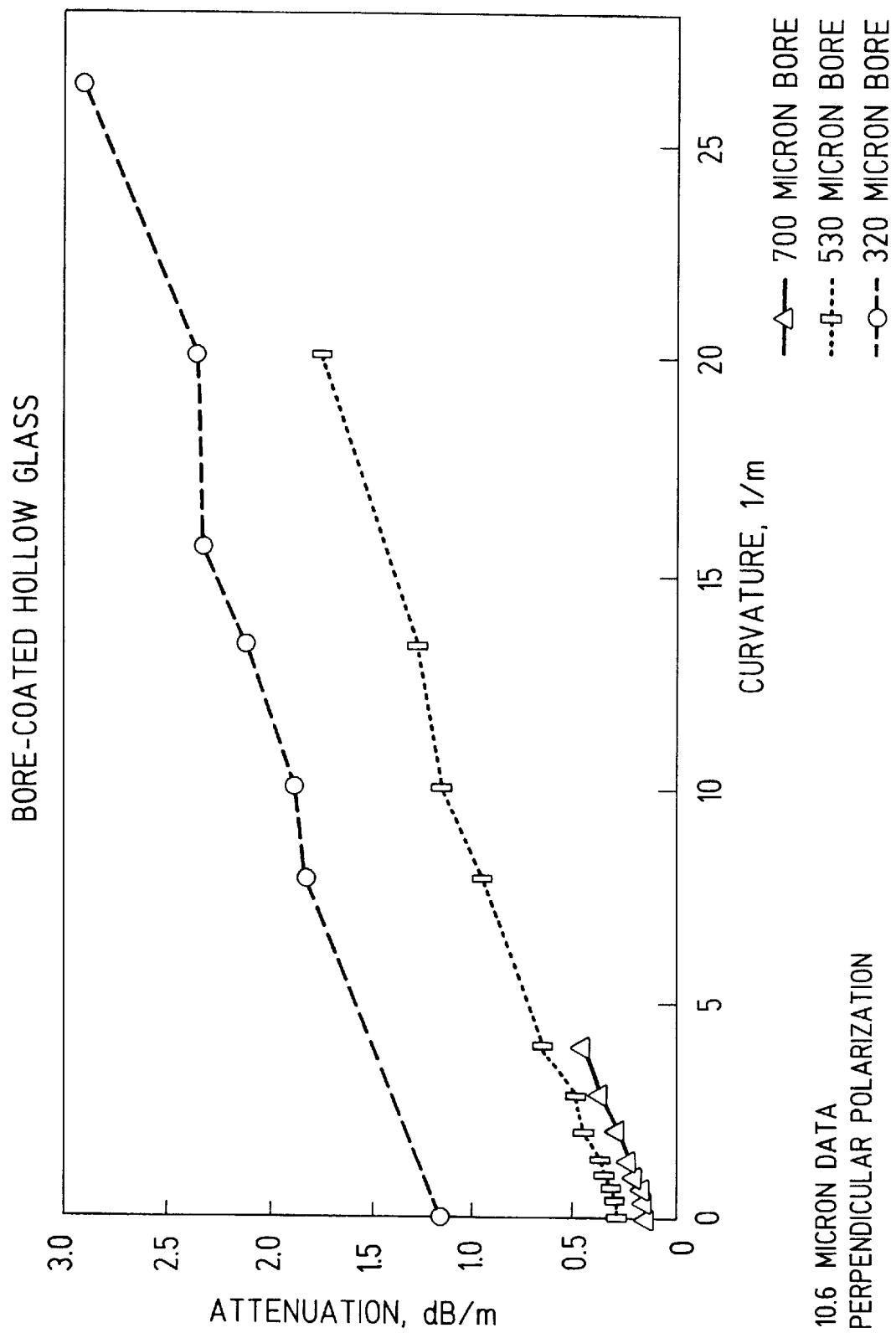
FIG. 5 is a graph of the performance vs. bending of several fibers, of differing bore sizes, constructed according to the present invention.
Figure 6:
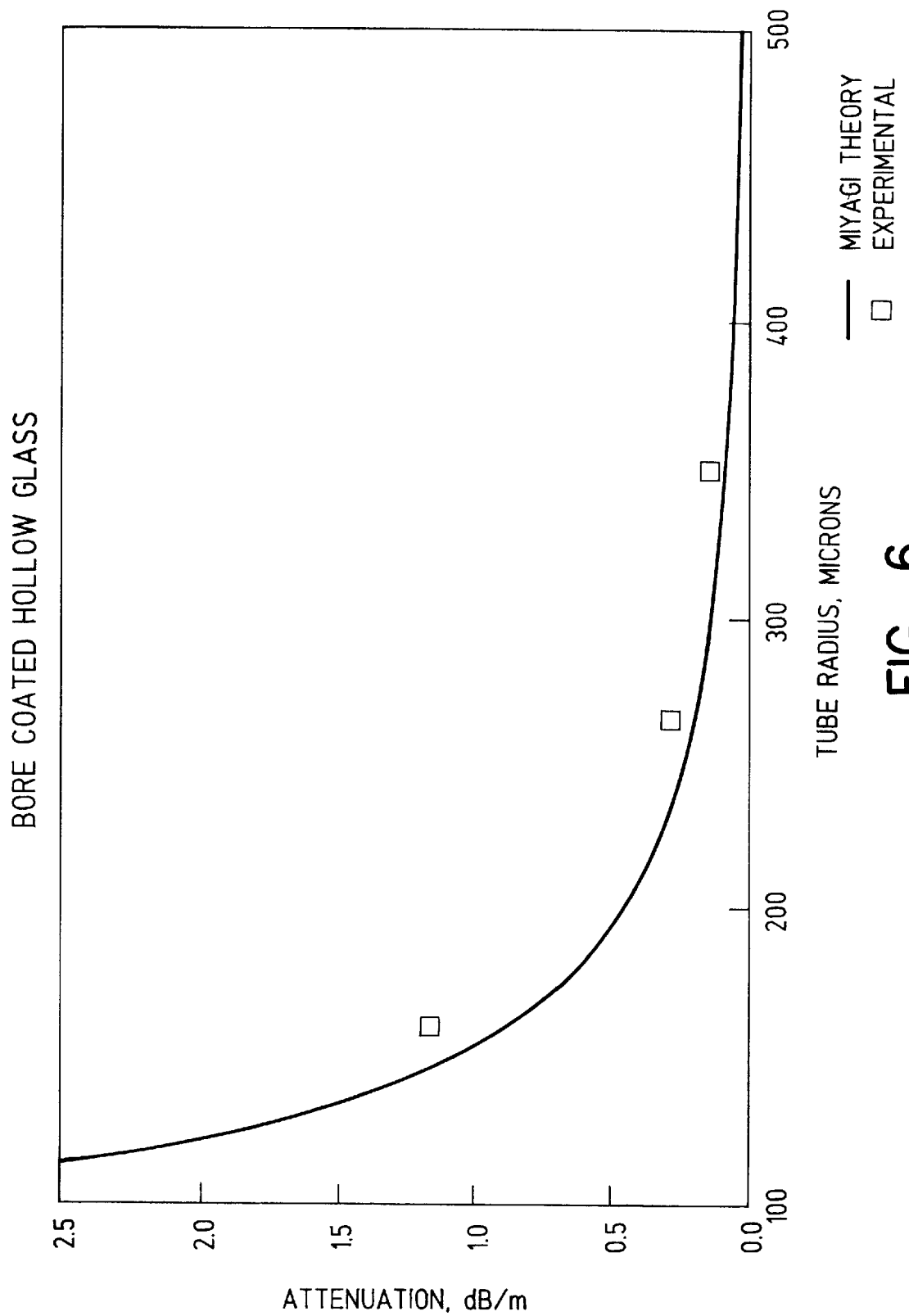
FIG. 6 is a graph illustrating how closely fibers constructed according to the present invention, approach the theoretical limit of performance.

FIGS. 5 and 6 demonstrate that the waveguides constructed according to the present invention exhibit attenuation near the theoretical limit. For comparison, waveguides constructed according to prior art techniques, such as the teachings of Croitoru et al. '863, are inferior by approximately 300 times.

Figure 7:
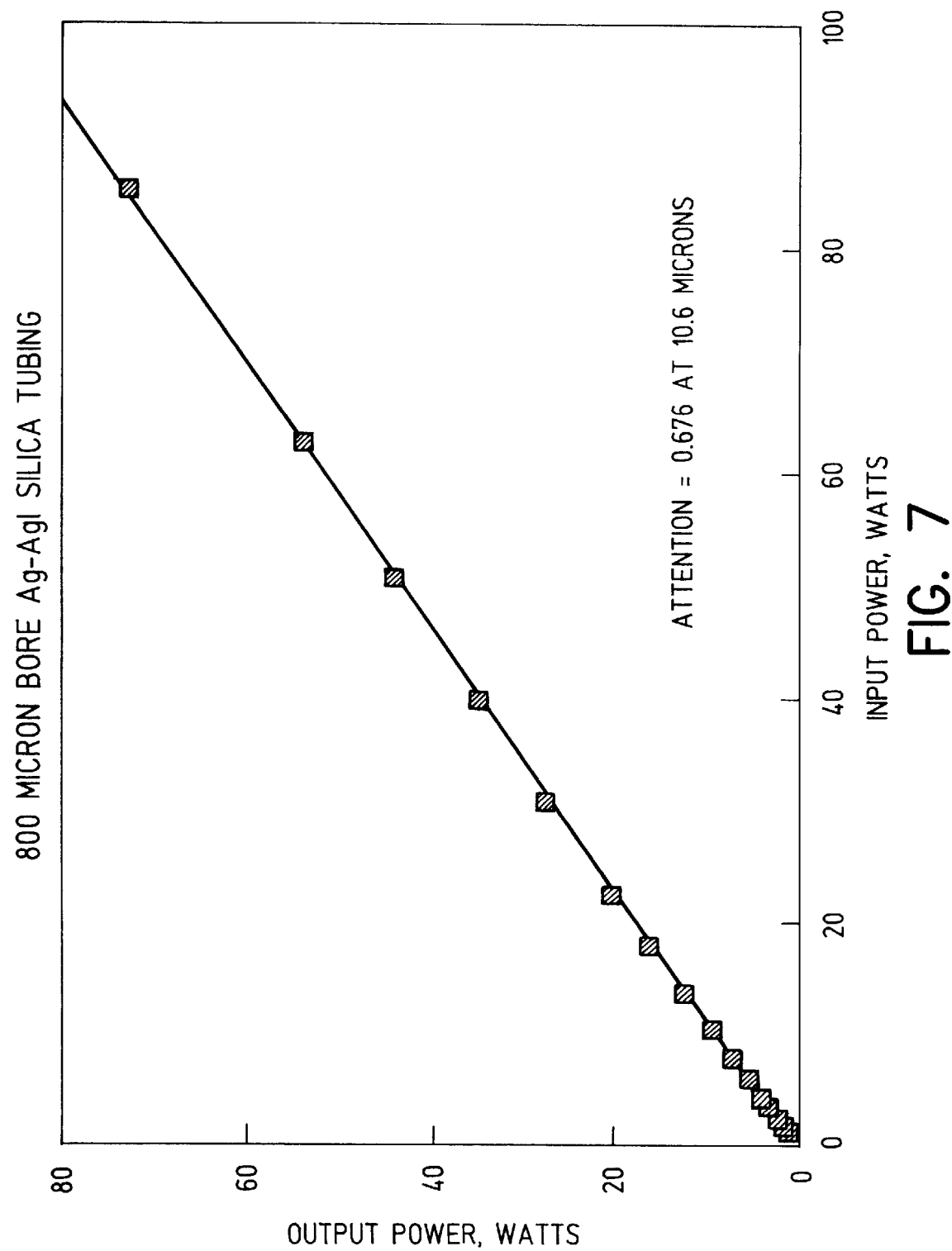
FIG. 7 is a graph illustrating the power-handling capability of a fiber constructed according to the present invention.

FIGS. 5 and 8 demonstrate the good flexibility and the low bending loss, and FIG. 7 demonstrates the power-handling capability, of waveguides 1 fabricated according to the present invention. Waveguides in accordance with the present invention have been measured to have losses as low as 0.1 dB/m for the 700-$\mu$m bore fibers and near single mode output. Waveguides in accordance with the present invention having inner diameters near 500-$\mu$m have losses as low as 0.3 dB/m when used with 9 $\mu$m lines of the $CO_2$ laser. At the Er:YAG laser wavelength of 2.94 $\mu$m, the loss is above 0.3 dB/m for waveguides having approximately a 700-$\mu$m inner diameter. A bend radius as small as 5 centimeters for a 500-$\mu$m bore is possible with a loss of only approximately 1.7 dB/m. The hollow glass waveguides of the present invention are about 275 times lower loss than a comparable prior art waveguide, such as is taught by Croitoru using plastic guides in U.S. Pat. No. 4,930,863. This is due, at least in part, to the ability of the present invention to maintain a very smooth exposed interior surface for the reflective layer 4 and the dielectric film 5. This results in low scattering loss and minimal mode conversion. The low loss of the present invention is also due in part to the fact that the dielectric thickness is carefully controlled. Further, no changes have been observed in their characteristics with time, and at least one such fiber performed well after hospital-grade sterilization with ethylene oxide. Rougher surfaces lead to higher loss, especially on bending. Furthermore, the present invention is rugged and can withstand substantial powers compared to the prior art plastic fibers, which can easily melt when transmitting powers over approximately 20 watts.

The present invention provides a simple structure which is fabricated using straightforward solution chemistry, and inexpensive flexible glass tubing. The present invention differs from the prior art in that the losses are very low due to the exceptional smoothness of the exposed inner surface of the bore of the waveguide of the present invention. The present invention also maintains a very high degree of flexibility, good transverse spatial coherence, and is non-toxic.

Figure 9:
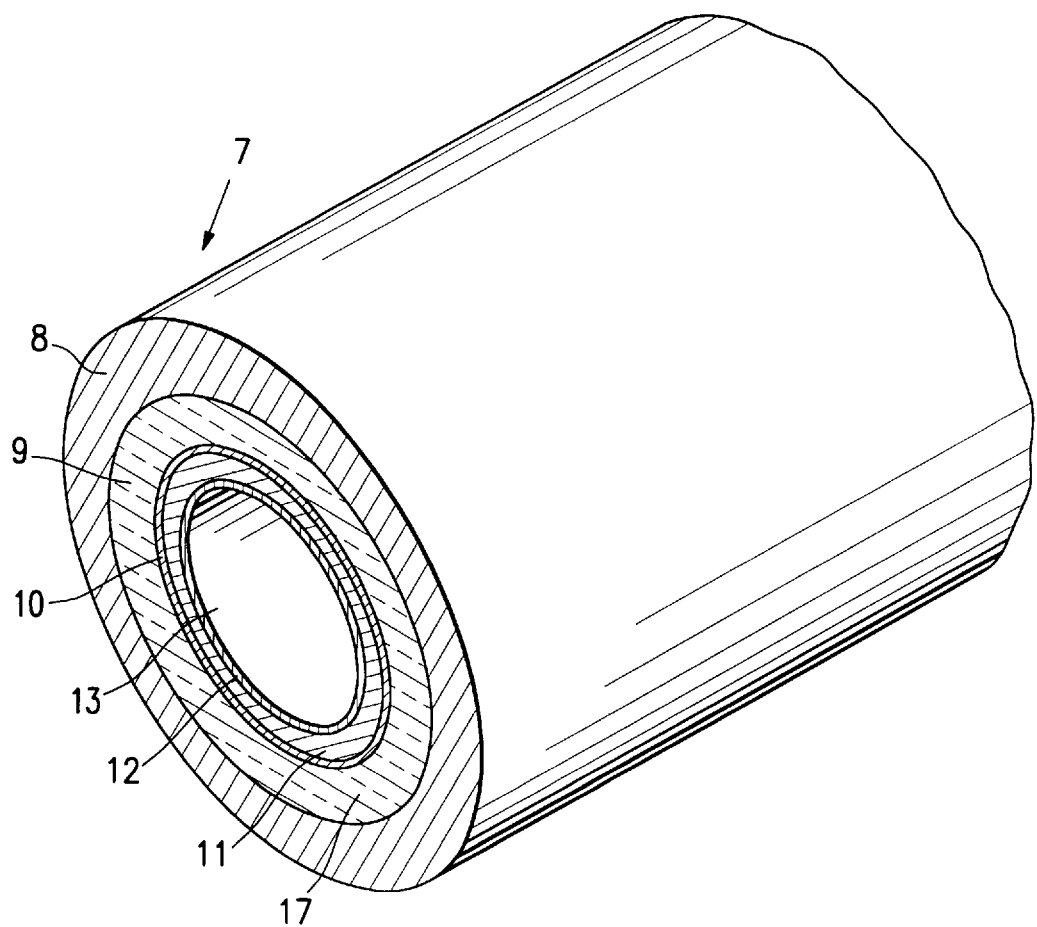
FIG. 9 is schematic end view of a first embodiment of the dual core waveguide according to the present invention, showing its construction.

FIG. 9 diagrammatically illustrates a double core waveguide 7, constructed according to an alternative embodiment of the present invention for transmitting both mid-infrared and near infrared through visible radiation from both incoherent and coherent sources. An outer cladding 8 is preferably formed around or onto the outer surface of the barrel of a hollow-fiber waveguide tube 9 having a smooth bore, such as commercially available thin-wall silica-glass tubing. The tube 9 forms an annulus which is used to carry radiation in the range of about 2.5 microns through the visible region. The waveguide 7 of the present invention is preferably of such thickness as to be suited to applications such as carrying cutting radiation to tissue sites within a human body. As such, the tube 9 of the present invention should have an outer diameter that permits the waveguide to be reasonably flexible. For example, it should be easily bent to a radius of less than about 10 centimeters. Outer cladding layer 8 provides a desired index of refraction at the outer surface of the tube 9, as described below. In order to protect the tube from abrasion and other mechanical degradation and to seal against moisture and other substances that physically degrade the tube 9, an outer protective sheath (not shown) may be provided. The sheath may be made of polymer coating, polyamide silicon/nylon, metal or other material. Alternatively, the sheath may replace the outer cladding 8 if it is configured to provide a desired index of refraction at the outer surface of the tube 9, as described below.

The tube 9 has an inner cladding layer 10 created at the surface of its interior bore. Both outer and inner cladding layers 8, 10 may be made by materials and processes such as fluorine doping, polymers, glass cladding, etc., applied by chemical vapor deposition (CVD), etc. The outer and inner cladding layers 8, 10 provide a material with the desired index of refraction to facilitate the transmission of light through the tube 9. In particular, the cladding layer 10 has an index of refraction of n1, the tube 9 has an index refraction of n2, and the outer cladding layer 8 has an index of refraction of n3. The materials of these three components are chosen so that n1 and n3 are both less than n2. In this way, light traveling through the tube 9 will encounter, on both outer walls, a material having a lower index of refraction than the tube 9. This will facilitate total internal reflection within the glass annulus.

A reflective layer 11 is deposited onto the inner cladding layer 10 in the bore of the tube 9 so as to retain a smooth exterior surface for the reflective layer 11, or such that the reflective layer 11 "levels" to a smooth reflective surface. The reflective layer is preferably silver of less than one micron in thickness. A dielectric film 12, preferably having an index of refraction that is less than the index of refraction of the reflective layer 11, is fabricated or deposited (i.e., "created") on the bore of the reflective layer 11 in a manner that substantially retains or improves the smoothness of the exposed surface of the bore. The dielectric film 12 enhances the reflectivity of the bore of the waveguide 7. The exact thickness of the dielectric film 12 is determined by optical measurements and is carefully controlled to give the lowest loss at a particular infrared wavelength. Preferably, the dielectric film 12 is approximately 0.1 micron to 0.8 microns thick. In the preferred embodiment, the dielectric film is silver iodide. However, in other embodiments, the dielectric film 12 may be made of inorganic compounds. The inner-exposed surface of the dielectric film 12 defines a preferably hollow interior volume 13 of the waveguide 7, which may contain air, another gas or gaseous mixture, vacuum, or any other medium, preferably having an index of refraction that is approximately equal to one.

It should be noted that the materials and fabrication techniques described herein for waveguide 1 in FIG. 1 may be used for waveguide 7 in FIG. 9 with the exception of the addition of the cladding layer 10 and the use of an outer layer 8 having an index of refraction less than the tube 9.

The cladding layer 10, the reflective layer 11 and the dielectric layer 12 are preferably thin and flexible. The waveguide 7 carries visible light through the transparent annulus of tube 9 with relatively low loss at frequencies between 2.5 microns and 0.25 microns.

In the preferred embodiment of the waveguide 7, the internal diameter of waveguide 7 prior to the application of the reflective layer 11 is from less than about 1.0 millimeter to about 100 microns, which provides good transmission characteristics, good mechanical flexibility, and is particularly suited for medical uses due to its size.

Using the present invention, approximately ten-meter long, hollow-fiber waveguides can be made having very low attenuation of infrared radiation 21 in its bore 13 and visible radiation 22 in its annulus tube 9. The bore (hollow interior volume 13) produces high transverse spatial coherence for mid-infrared wavelengths from about 2.0 microns to about 20 microns. For wavelengths between less than about 2.5 through the visible region, the tube 9 has low attenuation and good spatial coherence.

Figure 10:
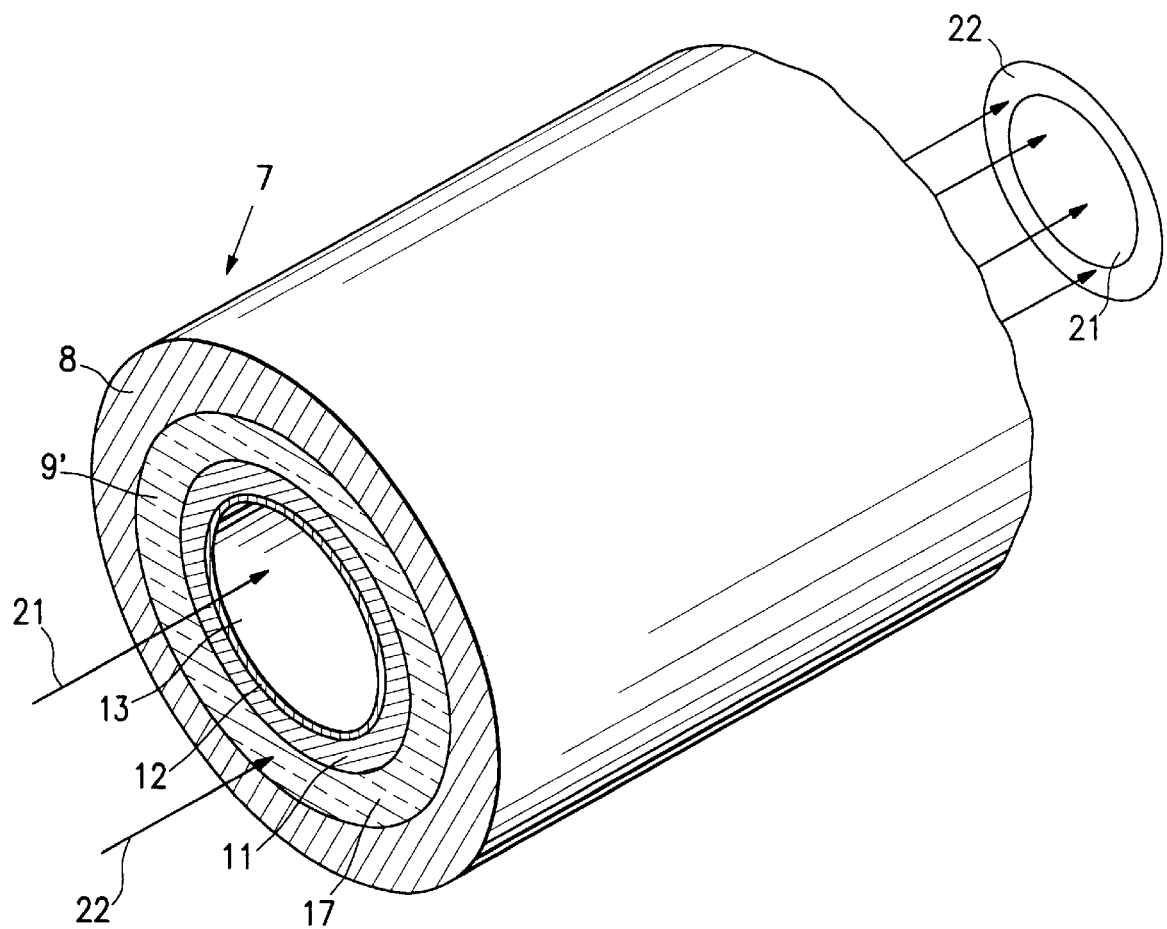
FIG. 10 is a schematic end view of a second embodiment of the dual core waveguide according to the present invention, showing its construction.

FIG. 10 diagrammatically illustrates a double core waveguide 14, constructed according to another embodiment of the present invention. This embodiment is similar to waveguide 7 in all respects except that instead of the inner cladding layer 10, there is a region 17 in the tube 9' having an index of refraction less than rest of the tube. Tube 9' is the same as tube 9 except for the region 17. Region 17 may be created by, for example, thermal diffusion implantation. The other components of waveguide 14 are the same as in waveguide 7, including outer cladding layer 8, reflective layer 11, dielectric film 12 and hollow interior volume 13.

EXAMPLE

The tube 9 of this embodiment of the present invention shown in FIGS. 9 and 10 is a smooth bore, thin-wall silica-glass tube. Such a tube is available from several commercial sources (e.g., Fiberguide Industries of Stirling, N.J. and Polymicro Technologies of Phoenix, Ariz.). Glass is preferred because of its high power handling capability (e.g., up to 500 watts of average power has been demonstrated) for the transmission of infrared through the bore. Glass is also preferred for the transmission of the visible and near infrared beam. Therefore, the same silica glass-tubing 3 of the embodiment of the waveguide 1 shown in FIG. 1, can also be utilized for the waveguide 7 in FIGS. 9 and 10. Nevertheless, other materials which are flexible, have the desired smoothness, and which easily transmit the desired wavelength, may also be used. These include, any other glass, plastic (PMMA), phosphate glasses, oxide glasses, non-oxide glasses, and sapphire.

In a preferred embodiment a fluorine-doped layer process is used to generate the outer and inner cladding layers 8, 10 at the inner and outer surfaces of the bore of the tube 9. The inner cladding layer 10 is then plated with a reflective layer 12 (such a silver, gold, copper, aluminum etc.) in a way that maintains the smoothness of the exposed surface of the reflective layer 4. A preferred plating process has been described in detail previously in the discussion of the reflective layer 4 of waveguide 1 in FIG. 1. Next, a smooth dielectric film 12 (preferably of silver iodide) having a predetermined index of refraction and an optimal thickness for the design wavelength, is formed on the surface of the reflective layer 11. The combination and implementation of these components as described herein is the novel method of the present invention, and produces the novel fiber waveguide 7 of this embodiment of the present invention.

In implementing the method of this embodiment of the present invention the previously discussed steps of pretreatment; etching/sensitizing/activating, silver solution, reducing solution, silver plating, and iodization, are essentially identical as those discussed previously for implementing the waveguide 1 shown in FIG. 1. In addition, as discussed above in connection with the waveguide 1 in FIG. 1, when a silver coating is used to form the reflective layer 4, the tubing 3 is coated with no pretreatment. However, in the present invention, prior to the silver coating, a cladding layer 10 is utilized on the inner surface of the tube 9 in order to alter the index of refraction characteristic near the inner surface of the tube 9. These outer and inner cladding layers 8, 10 have a lower index refraction than the tube 9. This will facilitate the total internal reflection of the electromagnetic beam passing though the body of the tube 9. For example, where the tube 9 will typically have an index refraction of about 1.5, the outer cladding layer 8 index may be 1.45, and that of the inner cladding layer 10 may be 1.45. It is preferred that the difference between the index of refraction of the inner and outer cladding layer be smaller than the tube 9 by between 0.1 and 10%.

In an alternative embodiment, shown in FIG. 10, the inner cladding layer 10, is replaced by a region 17 inside the glass tube 9. This region 17 has an index refraction that is less than that of the rest of the tube 9. In the preferred embodiment, this region 17 is formed by a thermal diffusion process.

Cladding Layer

In accordance with the preferred embodiment of the present invention, shown in FIG. 9, the generation of outer and inner cladding layers 8 and 10 is performed using a conventional fluorine doping procedure.

DISCUSSION

Figure 11:
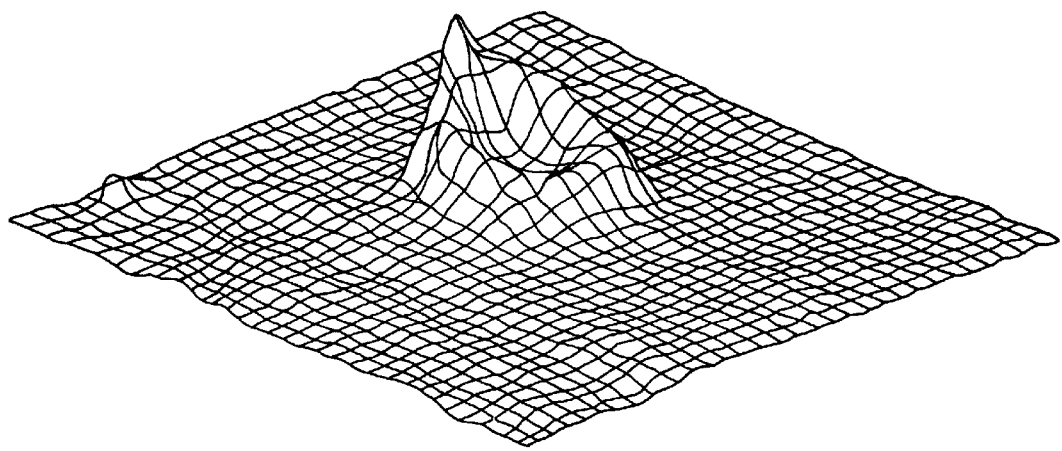
FIG. 11 is a graph of the three dimensional projection of the spatial profile of the power output from the dual core waveguide constructed according to the present invention, which is illuminated with a He Ne laser beam.

FIG. 11 demonstrates the excellent mode behavior of the transmission of visible light through the tube 9. The graph in FIG. 11 shows the light output for a helium neon laser at a wavelength of 0.6328 microns. In particular, this graph shows ring illumination. The peak on left side results from illuminating the tube 9 with a spot of light rather than using a ring of illumination matching the shape of the tube.

Figure 12:
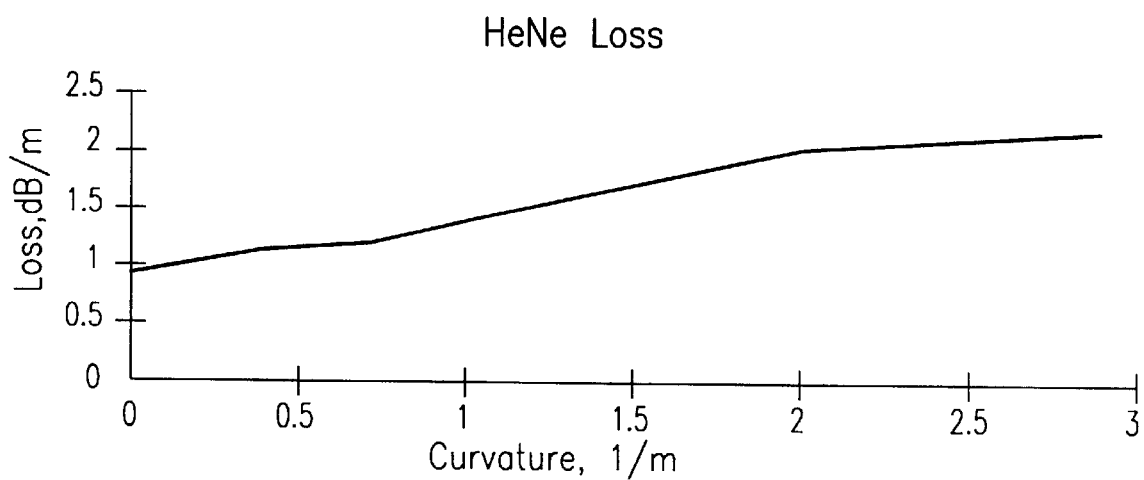
FIG. 12 is a graph of the spectral response of the dual core wavelength of the present invention versus the amount of bending of the waveguide, constructed according to the present invention.

FIG. 12 demonstrates the good flexibility and low bending loss of the transmission of the helium neon laser wavelengths through the tube 9. In particular, the loss of for a straight length of tube 9 is only 1.0 dB/m. At a curvature of about 2.8 m$^{-1}$, which corresponds to a bend radius of 0.36M, the loss at this wavelength increases to only about 2 dB/m. At near infrared wavelengths, such as Nd:YAG or Argon, the bending losses will be expected to be similar.

The waveguide 7 of the present invention provides a simple structure which is fabricated using straightforward solution chemistry, and an inexpensive, flexible tube 9. It provides the ability to deliver both a therapeutic infrared beam and a second beam (aiming and/or therapeutic) through the annular body of the tube 9. This reduces the necessity of having a separate, adjacent, waveguide for aiming the therapeutic beam. Furthermore, the waveguide 7 of the present invention allows a single laser delivery system to transmit a plurality of therapeutic wavelengths, thereby avoiding the duplication of delivery systems. Also, because the outer beam 22 delivers a visible annular ring aiming spot surrounding the IR therapeutic beam 21, a superior aiming beam is provided. This aiming beam, which is always aligned, gives the user a well defined view of the exact diameter of the invisible IR therapeutic beam 21. This can improve the visibility of the target spot prior to application of the therapeutic beam, since the target spot will not be illuminated, but will instead be in the center of the illuminated ring.

A number of embodiments of the present invention have been described. Nevertheless, it will be understood that various modifications may be made without departing from the spirit and scope of the invention. For example, a waveguide in accordance with one embodiment of the present invention has a protective outer coating or sheath about the barrel. In such an embodiment, the coating or sheath may be bonded to the waveguide. However, the waveguide of the present invention may alternatively be removably inserted into such a sheath. In another embodiment, the waveguide may be protected by a covering (commonly known as "heat-shrink tubing") which conforms to the outer surface of the waveguide upon an application of heat thereto. Furthermore, in applications in which the waveguide is used for a very limited time, such as medical applications, the waveguide may not be protected by any such coating. Any means for applying metal smoothly to the inner exposed surface of a hollow-fiber can be used to fabricate the waveguide of the present invention. Also, the solution that is used to deposit the reflective layer may be any reflective material, including metal alloys which include only one single metal. Furthermore, while the above description of the examples of the present invention focuses on the use of silver as the material used to fabricate the reflective layer, any material having a high reflectivity and capable of being smoothly deposited on the exposed inner surface of the bore of a hollow-fiber by flowing the material though the bore is within the scope of the present invention. Furthermore, any dielectric which has an appropriate index of refraction and which can be deposited on the exposed surface of the reflective layer is within the scope of the present invention. In addition, the inner cladding layer 10 may be replaced by other types of layers, or surface treatments, or even by an alternative tube 9 which has a desired internal gradient in index refraction to facilitate total internal reflection. Similarly, the outer cladding layer 8 surrounding the tube 9 can also be replaced by these alternative materials including a polymer sheath, to provide the desired index of refraction.

Accordingly, it is to be understood that the invention is not to be limited by the specific illustrated embodiment, but only by the scope of the appended claims.

What is claimed is:

1. A waveguide for transmitting a plurality of co-axial beams of electromagnetic radiation from at least one radiation source, comprising:

(a) a hollow, flexible tube having a transparent annular body surrounding a bore with a smooth inner bore surface; and (b) a reflective layer disposed upon the inner bore surface, wherein the bore transmits a first of said beams of electromagnetic radiation, and wherein the hollow, flexible tube transmits electromagnetic radiation from a second of said beams through its annular body.

2. The waveguide of claim 1 wherein said hollow, flexible tube is composed of glass.

3. The waveguide of claim 1 wherein said hollow, flexible tube is composed of plastic.

4. The waveguide of claim 1 further comprising a transition layer between the inner bore surface and the reflective layer having an index of refraction less than that of the annular body.

5. The waveguide of claim 4 wherein said transition layer is a fluorine-doped cladding layer.

6. The waveguide of claim 1 further comprising an outer cladding layer surrounding the hollow flexible tube.

7. The waveguide of claim 6 wherein said outer cladding layer has an index of refraction less than that of the annular body.

8. The waveguide of claim 7 wherein said outer cladding layer is a fluorine-doped layer.

9. The waveguide of claim 8 further comprising a transition layer between the inner bore surface and the reflective layer and having an index of refraction less than that of the annular body.

10. The waveguide of claim 7 wherein said outer cladding layer is composed of plastic.

11. The waveguide of claim 10 wherein said outer cladding layer is composed of silicone.

12. The waveguide of claim 1 wherein the annular body has a region of lower index of refraction near its surface than in areas further from said surface.

13. The waveguide of claim 12 wherein said region is formed by a thermal diffusion process.

14. The waveguide of claim 1 further comprising a dielectric film formed on said reflective layer.

15. A dual waveguide for transmitting first and second beams of electromagnetic radiation from at least one radiation source comprising:

(a) a hollow inner waveguide configured to transmit the first beam;

(b) an outer waveguide coaxial with said inner waveguide and configured to transmit the second beam, the outer waveguide having an annular cross-sectional shape.

16. The dual waveguide of claim 15 wherein said inner waveguide transmits infrared radiation.

17. The waveguide of claim 15 wherein the outer waveguide transmits visible light and wherein the visible light forms a visible annular ring around the first beam, whereby the location of the first beam can be ascertained.

18. A system for delivering therapeutic beams of electromagnetic radiation from at least one radiation source to a patient comprising:

(a) first and second beams of electromagnetic radiation;

(b) a hollow, flexible tube having a bore for transmitting a therapeutic beam therethrough, the hollow, flexible tube having an annular body transmitting a second beam of electromagnetic radiation therethrough.

19. The system of claim 18 wherein said first beam is a therapeutic beam and the second beam is visible light which facilitates aiming the therapeutic beam.

20. The system of claim 18 wherein both the first and second beams are therapeutic beams.

21. The system of claim 18 wherein said hollow, flexible tube annular body transmits either a therapeutic beam or a visible beam.

22. The system of claim 18 further comprising a third beam, wherein the hollow flexible tube annular body transmits both said second and third beams.

23. A method of manufacturing a waveguide for transmitting a plurality of beams of electromagnetic radiation, comprising:

providing a hollow, flexible tube having an index of refraction and a bore with a smooth bore surface;

coating the smooth bore surface to lower the index of refraction at the bore surface of the hollow flexible tube;

plating the coated bore surface with a reflective layer; and forming a dielectric film upon the reflective layer.

24. The method of claim 23 further comprising the step of coating an internal surface of the bore with a fluorine-doped layer.

25. The method of claim 23 wherein said hollow, flexible tube is composed of silica.

26. The method of claim 23 further comprising the step of depositing a cladding layer around the exterior of said hollow, flexible tube.

27. A method for delivering therapeutic electromagnetic radiation from a radiation source to a destination comprising:

transmitting a first beam of electromagnetic radiation through the bore of a hollow, flexible tube having an annular body; and transmitting a second beam of electromagnetic radiation through the annular body of the hollow, flexible tube.

28. The method of claim 27 wherein said second beam is visible light and said first beam is infrared electromagnetic radiation.

29. The method of claim 28 wherein the first beam is a therapeutic beam and the second beam facilitates aiming the therapeutic beam.

30. The method of claim 27 wherein both the first and second beams are therapeutic beams.

31. The method of claim 27 further comprising transmitting a third beam of electromagnetic radiation through the annular body of the hollow, flexible tube.

32. A method of manufacturing a waveguide for transmitting a plurality of beams of electromagnetic radiation from a radiation source to a destination, comprising:

providing a hollow, flexible tube having an index of refraction and a bore with a smooth bore surface;

treating a transition region of the hollow, flexible tube near the smooth bore surface to lower the index of refraction near the bore surface region of the hollow flexible tube;

plating the bore surface with a reflective layer; and forming a dielectric film upon the reflective layer.

* * * * *